United States Patent [19]
Zhong et al.

[11] Patent Number: 5,767,368
[45] Date of Patent: Jun. 16, 1998

[54] METHOD FOR PRODUCING A CEREAL PLANT WITH FOREIGN DNA

[75] Inventors: Heng Zhong, East Lansing; Masomeh B. Sticklen, Okemos, both of Mich.

[73] Assignee: Board of Trustees operating Michigan State University, East Lansing, Mich.

[21] Appl. No.: 415,426

[22] Filed: Apr. 3, 1995

[51] Int. Cl.$^6$ .......................... C12N 15/29; C12N 15/82; A01H 4/00; A01H 5/00

[52] U.S. Cl. .................................... 800/205; 800/DIG. 56; 435/172.3; 435/320.1; 435/413; 435/418; 435/419; 435/424; 435/430; 435/431; 536/236; 536/237; 536/24.1

[58] Field of Search ........................... 435/172.3, 240.4, 435/320.1, 240.45, 240.5, 413, 418, 419, 424, 430, 431; 800/205, DIG. 56; 536/23.6, 23.7, 24.1

[56] References Cited

U.S. PATENT DOCUMENTS

| | | | |
|---|---|---|---|
| 5,281,529 | 1/1994 | Zhong et al. | 435/240.45 |
| 5,320,961 | 6/1994 | Zhong et al. | 435/240.45 |

OTHER PUBLICATIONS

M.E.Fromm, et al., Bio/Technology, 8:833–839 (1990).
W. J. Gordon–Kamm, et al.,Plant Cell, 2:603–618 (1990).
Wang, Y.C., et al., Plant Biol. 11:433–439 (1988).
Christou, P., The Plant Journal 2:275–281 (1982).
Kartha, K.K., et al., Plant Cell Rep. 8:429–432 (1989).
Walters, D.V., et al., Plant Mol. Biol. 18:189–200 (1992).
Christou, P., et al., Bio/Techonology 9:957–962 (1991).
Vasil, V., et al., Bio/Technology 10:667–674 (1992).
Rhodes, C. A., et al., Science 240:204–207 (1988).
Murry, L.E., et al., Bio/Technology 11:1559–1564 (1993).
Vain, P., et al., Plant Cell Reports 12:84–88 (1993).
Koziel, M.G., et al., Plant Cell 11:194–200 (1993).
Laursen, C.M., et al., Plant Mol. Biol. 24:51–60 (1994).
D'Halluin, K., et al., Plant Cell 4:1495–1505 (1992).
Golovkin, M.V., et al., Plant Sci 90:41–52 (1993).
Omirulleh, S., et al., Plant Mol. Biol. 21:415–428 (1993).
Zhong, et al., Planta 187:483–489 (1992).
Zhong, et al., et al., Planta 187:490–497 (1992).
Steeves, T.A., et al., Patterns in Plant Development 2nd ed. (NY:Cambridge Univ. Press) (1989) pp. 46–61.
Medford, J.I., Plant Cell, 4:1029–1039 (1992).
McCabe, D.E., et al., Bio/Technology 11:596–598 (1993).
Brar, G.S., et al., Plant J. 5:(5):745–753 (1994).
Bidney, D., et al., Plant Mol. Biol. 18:301–313 (1992).
Christou, P., et al., Trends in Biotech 8:145–151 (1990).
Jefferson, R.A., Plant Mol. Biol. Rep. 5:387–405 (1987).
Oard, J.H., et al., Plant Physiol. 92:334–339 (1990).
Bilang, R. Zhang, et al., Transient gene expression in after ballistic microtargeting 4(4);735–744 (1993).
Iglesias, V.A. et al., Planta 192:84–91 (1994).
Dupuis, I., et al., Plant Cell Reports 12:607–611 (1993).
Simmonds, J.A., et al., Plant Physiol. 85:197–206 (1992).
Ahokas, H., Theor. Appl. Genet. 77:496–472 (1989).
Schlappi, M., et al., Plant Cell 4:7–16 (1992).
Grimsley, N., et al., Bio/Technology 6:185–189 (1988).
Gould, J., et al., Plant Physiol. 95:426–434 (1991).
McDaniel, C.N., et al., 175:13–22 (1988).
Thompson, C.J., et al., EMBO J 6:2519–2523 (1987).
Keil, M., et al., Nucleic Acids Research 14:5641–5650 (1986).
Bevan, M., et al., Nucleic Acid Res. 11:369–385 (1983).
McElroy, D., et al., Plant Cell 2:163–171 (1990).
Potrykus 1990 Bio/Technology 8:535–542.
Potrykus 1991 Ann Rev Pl Physiol Pl Mol. Biol. 42:205–225.
Gordon–Kamm 1991 In Vitro Cell Dio. Biol. 27P:21–27.
Maheshwari et al. 1995 Critical Reviews in Pl. Sci. 14(2):149–178.
Ayres et al. 1994 Critical Reviews in Plant Sciences 13(3):219–239.
McElroy et al. 1994 Trends in Biotechnology 12:62–68.
Cao et al. 1990 In Plant Gene Transfer, Lamb et al. (eds), Wiley–Liss, pp. 21–34.
Gambley et al. 1993 Plant Cell Reports 12:343–346.
Perez–Vicente et al. 1993 J Plant Physiol 142:610–617.
Cao et al. 1992 Plant Cell Reports 11:586–591.

*Primary Examiner*—Douglas W. Robinson
*Assistant Examiner*—Thomas Haas
*Attorney, Agent, or Firm*—Ian C. McLeod

[57] ABSTRACT

A method for isolating a cereal plant with foreign DNA by bombarding meristem primordia tissue with particles coated with the foreign DNA in a culture media is described. The foreign DNA in the transformed plants can provide proteins which impart disease and/or insect resistance or other desirable properties.

15 Claims, 5 Drawing Sheets

METHOD FOR PRODUCTING A CEREAL PLANT WITH FOREIGN DNA

GOVERNMENT RIGHTS

This application was funded under U.S. Agency For International Development Contract No. USAID DAN4197-A-00-1126-00. The U.S. Government has certain rights under this invention.

BACKGROUND OF THE INVENTION

1. Field of the Invention

The present invention relates to a method for producing a cereal plant with foreign DNA, particularly DNA encoding a protein which provides disease and/or insect resistance, using micro projectile bombardment of meristem primordia. In particular, the present invention relates to a method which produces maize containing the foreign DNA.

2. Description of Related Art

Significant progress has been made in the stable genetic transformation and regeneration of corn via microprojectile bombardment (M. E. Fromm, F. Morrish, C. Armstrong, R. Williams, J. Thomas and T. M. Kelin, Bio/Technology, 8 833–839 (1990); and W. J. Gordon-Kamm, T. M. Spencer, M. L. Mangano, T. R. Adams, R. J. Daines, W. G. Start, J. V. O'Brian, S. A. Chambers, Jr., W. R. Adams, N. G. Willets, T. B. Rice, C. J. Mackey, R. W. Krueger, A. P. Kaush and P. G. Lemaux, Plant Cell, 2 603–618 (1990)).

High velocity microprojectile bombardment has been demonstrated to deliver DNA into embryos or suspension culture cells of most cereal crops (Wang, Y.C., Klein, T. M., Fromm, M., Cao, J., Sanford, J. C. and Wu, R., Plant Mol. Biol. 11, 433–439 (1988); Christou, P., The Plant Journal 2, 275–281 (1992); and Kartha, K. K., Chibbar, R. N., Georges, F., Leung, B., Caswell, K., Kendall, E. and Qureshi, J., Plant Cell Rep. 8 429–432 (1989)). Microprojectile bombardment has been successfully used to obtain transgenic plants in maize (Fromm, M. E., Morrish, F., Armstrong, C., Williams, R., Thomas, J. and Klein, T. M., Bio/Technology 8, 833–839 (1990); Gordon-Kamm, W. J., Spencer, T. M., Mangano, M. L., Adams, T. R., Daines, R. J., Start, W. G., O'Brian, J. V., Chambers, S. A., Adams, Jr., W. R., Willets, N. G., Rice, T. B., Mackey, C. J., Krueger, R. W., Kaush, A. P. and Lemaux, P. G., Plant Cell 2, 603–618 (199); and Walters, D. V., Vetsch, C. S., Potts, D. E. and Lundquist, R. C., Plant Mol. Biol. 18, 189–200 (1992)), rice (Christou, P., Ford, T. L. and Kofron, M., Bio/Technology 9, 957–962 (1991)) and wheat (Vasil, V., Castillo, A. M., Fromm, M. E. and Vasil, I. K., Bio/Technology 10, 667–674 (1992)).

More than a decade of arduous and substantial effort has resulted in the production of recalcitrant maize plants. The infertile transgenic maize plants were recovered via electroporation of protoplasts (Rhodes, C. A., et al., Science 7 204–207 (1988)). Fertile transgenic maize plants were subsequently produced via microprojectile bombardment of embryogenic calli or cell suspensions (Gordon-Kamm, W. J., et al., Plant Cell 2 603–618 (1990); Fromm, M. E., et al., Bio/Technology 8 833–839 (1990); Walter, D. A., et al., Plant Mol. Biol. 18 189–200 (1992); Murry, L. E., et al., Bio/Technology 11 1559–1564 (1993); and Vain, P., et al., Plant Cell Reports 12 84–88 (1993)) and immature embryos (Koziel, M. G., et al., Plant Cell 11 194–200 (1993)); electroporation of cell suspensions (Laursen, C. M., et al., Plant Mol. Biol. 24 51–60 (1994)) and enzymatically treated immature embryos or mechanically wounded callus (D'Halluin, K., et al., Plant Cell 4 1495–1505 (1992)), silicon carbide whisker-mediated transformation of cell suspensions (Frame, B. R., et al., Plant Journal 6,001–6,008 (1994)), and PEG-mediated transformation of protoplasts (Golovkin, M. V., et al., Plant Sci 90 41–52 (1993); and Omirulleh, S., et al., Plant Mol. Biol. 21 415–428 (1993)). Among these four methods, the microprojectile bombardment has been demonstrated to be more adaptable to explant sources of cereal crops than the other methods in terms of delivery of DNA into cells and recovery of fertile transgenic plants (Christou, P., Plant J. 8 275–281 (1992)). However, microprojectile bombardment is restricted to particular tissues from certain maize genotypes which are adapted to an in vitro regeneration system. Therefore, the development of an easy, rapid, and more genotype-independent regeneration and transformation method is needed, without the time-consuming and labor-intensive in vivo immature embryo preparation and the in vitro tissue culture manipulation.

Previous research on maize morphogenesis demonstrated that the corn meristem is morphogenetically plastic and can be manipulated genotype-independently to produce multiple shoots, somatic embryos, tassels or ears by a simple variation in in vitro culture condition (Zhong, et al., Planta 187 483–489 (1992); Zhong, et al., Planta 187 490–497 (1992); U.S. Pat. Nos. 5,281,529 and 5,320,961). There is a need for efficient transformation.

Shoot tip, or shoot apex, consists of the shoot apical meristem, the formation region of lateral organ primordia, the subapical enlargement region of shoot and primordia, and the several leaf primordia (Steeves, T. A. and Sussex, I. M., Patterns in Plant Development, 2nd ed. (New York: Cambridge University Press) (1989)). Shoot apical meristem comprises the initial cells and the subepidermal cells which initiates the germ line cells of tissue and organ (Medford, J. I., Plant Cell, 4 1029–1039 (1992)). Theoretically, there are two possibilities for recovering transgenic plants via transfer DNA into shoot apical meristem. One is that the transgenic progeny is directly produced via transformation of the subepidermal cells or/and the germ line cells which participate in floral formation, followed by the development of a partially transgenic reproductive organ, the gametophyte cells as the foreign carrier. Due to this nature of the transformation method, the parent plants will always be chimeric. In such system, it is very difficult to use any selectable marker, such as antibiotics and herbicides, to improve transformation frequency and to recover transgenic progenitor other than using reporter marker, such as β-glucuronidase and anthocyanin biosynthesis, to screening the original transformants. Such approaches have been successfully made in several dicotyledonous species including soybean (McCabe, D. E., et al., Bio/Technology 6 923–926 (1988)), cotton (McCabe, D. E., et al., Bio/Technology 11 596–598 (1993)), peanut (Brar, G. S., et al., Plant J. 5(5) 745–753 (1994)) and sunflower (Bidney, D., et al., Plant Mol. Biol. 18 301–313 (1992)) via particle bombardment or combination with Agrobacterium-mediated transformation of shoot meristem which resulted in the commercial applications of genotype-independent transformation of soybean (Christou, P., et al., Trands Biotech 8 145–151 (1990)) and peanut (Brar, G. S., et al., Plant J. 5(5) 745–753 (1994)). However, the application of such advanced methods in cereal transformation is still unsuccessful although numerous attempts have been made during the last few years. Transient or stable gene expression in cereal was reported after delivery of DNA into cells of cereal shoot apex or tassel primordia via microprojectile bombardment (Oard, J. H., et al., Plant Physiol. 92 334–339 (1990); Bilang, R. Zhang, et al., Transient gene expression in vegetative shoot apical meristems of wheat after ballistic microtargeting 4(4) 735–744 (1993); Iglesias, V. A., et al., Planta. 192 84–91 (1993); Dupuis, I., et al., Plant Cell Reports 12 607–611 (1993)), microinjection (Simmonds, J. A., et al., Plant Physiol. 85 197–206 (1992)), electrophoretic transfection (Ahokas, H., Theor. Appl. Genet. 77 496–472 (1989)), and Agrobacterium-mediated transformation (Schlappi, M., et al., Plant Cell 4 7–16 (1992); Grimsley, N., et al., Bio/Technology 6 185–189 (1988); and Gould, J., et al., Plant Physiol. 95 426–434 (1991)). The reasons of such failure occurred in cereal meristem transformation are not only because of the poor efficiency of both regeneration and transformation as compared to which in dicotyledonous, but also because the technical difficulty of both localizing and distinguishing the germline cells and apical meristem cells, which contribute to plant floral organs, from extremely small and highly organized shoot tips. Moreover, it is also because few understanding of the fundamental development of these cells even though the approach so far indicated that about 15 L2 cells from shoot apical meristem of the germinating maize embryo may contribute to tassel formation (McDaniel, C. N., et al., 175 13–22 (1988)).

OBJECTS

It is therefore an object of the present invention to provide a method for producing a cereal plant with foreign DNA. Further, it is an object of the present invention to provide the cereal plant, particularly maize, with the DNA which encodes a protein providing disease and/or insect resistance in the plant. In particular, it is an object of the present invention to provide a method which is relatively simple and economical. These and other objects will become increasingly apparent by reference to the following description and the drawings.

IN THE DRAWINGS

The file of this patent contains at least one drawing executed in color. Copies of this patent with color drawings (s) will be provided by the Patent and Trademark Office upon request and payment of the necessary fee.

FIG. 3A shows southern blot hybridization of R0 transgenic maize plants containing the potato protease inhibitor II (pin2) gene regulated by the wound-inducible pin2 promoter and the rice actin (ActI) intron. Lanes 1–3, 10 pg of pTW-a plasmid DNA; Lanes 4–6, 10 µg of genomic DNA from untransformed maize plant; Lanes 7–21, 10 µg of genomic DNA from putative transgenic maize plants; Lanes 7–9, plant MCT-1; Lanes 10–12, plant MCT-2; Lanes 13–15, plant MCT-3; Lanes 16–18, plant MCT-5; Lanes 19–21, plant MCT-6,; Lanes 1, 4, 7, 10, 13, 16 and 19, DNA undigested; Lanes 2, 5, 8, 11, 14, 17 and 20, DNA digested with Hind III; Lanes 3, 6, 9, 12, 15, 18, and 21, DNA digested with Eco RV. The P-32 labeled probe was the 1.5 kb gel isolated XbaI fragment of pTW-a containing the pin2 coding region and terminator. FIG. 3B shows southern blot hybridization of R0 transgenic maize plants containing the bar gene. Lanes 1–3, 10 µg of pTW-a plasmid DNA; Lanes 4–6, 10 µg of genomic DNA from untransformed maize plant; Lanes 7–21, 10 µg of genomic DNA from putative transgenic maize plants; Lanes 7–9, plant MCT-1; Lanes 10–12, plant MCT-2; Lanes 13–15, plant MCT-3; Lanes 16–18, plant MCT-5; Lanes 19–21, plant MCT-6. Lanes 1, 4, 7, 10, 13, 16 and 19, DNA undigested; Lanes 2, 5, 8, 11, 14, 17 and 20, DNA digested with Eco RI; Lanes 3, 6, 9, 12, 15, 18 and 21, DNA digested with Eco RV. The P-32 labeled probe was the 0.6 kb gel isolated from Sma I fragment of pTW-a. FIG. 5C shows plasmid pTW-a containing pin2-Act1 intron fusion gene (pin2 promoter, rice Act1 intron, pin2 coding region and pin2 terminator) and bar gene (CaMV 35S promoter, bar coding region and nos terminator) in pUC vector.

DESCRIPTION OF PREFERRED EMBODIMENTS

The present invention relates to a method for producing a cereal plant material with foreign DNA which comprises providing isolated shoot apex meristem primordia of the plant in a first culture medium which has been cultured in the medium for a sufficient time with subculturing to allow the meristem primordia to be transformed with the foreign DNA; bombarding the meristem primordia with micron sized particles coated with the foreign DNA to transform the meristem primordia with the DNA; growing the bombarded meristem primordia in a second culture medium; and regenerating the meristem primordia containing the foreign DNA to produce the cereal plant material.

The regeneration of transgenic maize plants achieved in this invention allows the genetic improvement of this important crop using microprojectile bombardment. High regenerative competence of the bombarded meristem combined with high level of expression driven by the rice actin 1 5' sequences contributed to the recovery of transgenic maize without any selection pressures.

An efficient, reproducible and highly genotype-independent method for the rapid recovery of independent fertile transgenic maize plants was developed. The transformation was particularly performed using the high-velocity microprojectile bombardment of the cultured, isolated, shoot apex primordia of maize with a plasmid carrying the two linked genes, bar and pinII, each driven by a different promoter, or a plasmid containing Act 1-gus fusion gene, or with combination with both plasmids. The bombarded shoot apices were subsequently multiplied and selected under 3–5 mg/l glufosinate-ammonium (IGNITE) for the bar gene for PAT activity. From 146 independent transgenic meristem clumps recovered from 39 petri dishes, thousands of fertile transgenic plants carrying either linked or unlinked genes were consistently regenerated under continuous selection using 5–10 mg/l glufosinate-ammonium. The transformation frequencies were 100% and 83% on average for linked and unlinked genes, respectively. The average co-expression frequency of bar (PAT activity) and gus genes was about 56%. The integration and the inheritance of bar, pinII as well as gus in transgenic R0 and R1 plants were confirmed.

The confirmation of functional activity of phosphinothricin acetyltransferase (PAT) was performed by localized application or spraying of 1% of IGNITE herbicide to transgenic R0 and R1 plants. The localized expression of Acti-gus protein in the R0 and R1 plants was extensively analyzed by histochemical assay and fluorescence assay, respectively. The highest gus expression was found in all meristematic tissues or organs such as shoot meristem, axillary bud region, leaf primordium, root tip, floral or spikelet primordium, immature embryo and vascular system. Bar and pin2 were detected using insects and protein assays.

The culture medium preferably contains a cytokinin and preferably an auxin. The auxins which are particularly useful are 3,6-dichloro-o-anisic acid (dicamba); 2,4-dichlorophenoxyacetic acid (2,4-D); indole-3-acetic acid (IAA); indole-3-butyric acid (IBA); and α-naphthaleneacetic acid (NAA) at a concentration between about 0.001 to 10 μM. The cytokinins which are particularly useful are 6-benzylaminopurine (or 6-benzyladenine) (BAP (or BA)); 6-furfurylamino-purine (Kinetin); and 6-(4-hydroxy-3-methylbut-2-enylamino)purine (Zeatin) at 0.001 to 10 μM. The preferred culture medium contained BA at 0.01 to 10 μM and 2,4-D at 0 to 10 μM. The method preferably uses MS medium (Sigma Chemicals, St. Louis, Mo.) containing 0 to 5 μM 2,4-dichlorophenoxyacetic acid and 0.01 to 10 μM 6-benzylaminopurine (BA). Casein hydrolysate is preferably used in an amount between 0.5 and 1 g/l. This type of medium is described in U.S. Pat. No. 5,281,529 to the present inventors.

The β-glucuronidase under the control of rice actin regulatory sequences was used as a marker. Histochemical assays of samples from meristem demonstrated β-glucuronidase enzymatic activity. Putatively transgenic plants regenerated from these cultures displayed a band of the appropriate size following Southern blot hybridization of polymerase chain reaction amplified DNA. Southern analysis of restriction digested genomic DNA also showed the presence of positive signals in all of the screened plants. Polymerase chain reaction-amplified cDNA and Western blot analysis of these transformed plants revealed the synthesis of β-glucuronidase mRNA and protein.

The transformation of maize with the microprojectile bombardment of meristem followed by the regeneration of transgenic plants is described herein.

MATERIALS AND METHODS

The MS basal medium cultured onto agar-solidified basal medium (MS-M5519) contained:

| | |
|---|---|
| Ammonium Nitrate | 1650.0 |
| Boric Acid | 6.2 |
| Calcium Chloride (Anhydrous)* | 332.2 |
| Cobalt Chloride-6H$_2$O | 0.025 |
| Cupric Sulfate-5H$_2$O | 0.025 |
| Na$_2$-EDTA | 37.26 |
| Ferrous Sulfate-7H$_2$O | 27.8 |
| Magnesium Sulfate (Anhydrous)** | 180.7 |
| Manganese Sulfate-H$_2$O*** | 16.9 |
| Molybdic Acid (Sodium salt) -2H$_2$O | 0.25 |
| Potassium Iodide | 0.83 |
| Potassium Nitrate | 1900.0 |
| Potassium Phosphate Monobasic | 170.0 |
| Zinc Sulfate-7H$_2$O | 8.6 |
| Glycine (free base) | 2.0 |
| Myo-Inositol | 100.0 |
| Nicotinic Acid (free acid) | 0.5 |
| Pyridoxine HCl | 0.5 |
| Thiamine-HCl | 0.1 |
| Grams of powder to prepare 1 liter | 4.4 |

*Original formula contains calcium chloride dihydrate at 440.0 mg/L.
**Original formula contains magnesium sulfate heptahydrate at 370.0 mg/L.
***Original formula contains manganese sulfate tetrahydrate at 22.30 mg/L.

Any transgenic apical meristem cells of cereal plants can be reprogrammed in the developmental direction under in vitro conditions. The transgenic cereal plants can be regenerated from these cells with or without selection. The maize meristem was transformed via the microprojectile bombardment with a series of chimeric genes including a herbicide resistant gene (bar) insect resistant genes, pin 2 and synthetic CryIA(b), based upon a Bacillus thurengensis, and a reporter gene, uid A (gus).

The efficient recovery of fertile transgenic maize plants was achieved via the highly genotype-independent shoot multiplication systems after the microprojectile bombardment of shoot tips. The maize shoot apices were transformed with a plasmid incorporating bar and pin 2, driven by caMV 35S promoter and wound-inducible pin2 promoter, respectively, either alone or in combination with another plasmid containing uid A (gus), driven by rice actin 1 promoter. The integration and the inheritance of linked and unlinked genes in transgenic R0 and R1 maize plants were confirmed. The functional activity of Act1-gus and 35S-bar in transgenic R0 and R1 plants was extensively analyzed.

Plant Materials

Following the previous work on shoot multiplication (Zhong, H., et al., Planta 187 483–489 (1992)), another 16 genotypes in addition to the previous 20 genotypes of maize (*Zea mays* L.) were tested and all responded to form multiple shoot clumps. Mature kernels of 12 genotypes (Tables 1 and 2) were randomly selected for this research. The kernels were surface-sterilized with 70% ethanol and 2.6% sodium hypochlorite, and germinated on the MS basal medium as described before (Zhong., H., et al., Planta 187 483–489 (1992)). A 5 mm-long section of seedling containing a shoot tip, leaf primordia and a portion of young leaves and stem proximal to shoot tip were excited, cultured in darkness for four weeks and maintained in light at four-week intervals on the shoot multiplication medium composed of MS basal medium, 500 mg/l casein hydrolysate (CH) and 9 µM $N_6$-benzyladenine(BA) with or without 2.25 µM 2,4-dichlorophenoxyacetic acid (2,4-D), designed as CSMD and CSM, respectively (Zhong, H., et al, Planta 187 483–489 (1992)).

Because the sweet corn genotypes, Honey N pearl (HNP) and Illinois Golden Xtra Sweet (IGXS), were the model materials for morphogenesis study, the shoot multiplication cultures of these two genotypes were also used for this experiment.

Plasmids

The plasmid pTW-a (7.4 kb) (FIG. 5C) containing a herbicide-resistant gene, bar (Thompson, C. J., et al., EMBO J. 6 2519–2523 (1987)) and an insect-resistant gene, pin2 (Keil, M., et al., Nucleic Acids Research 14 5641–5650 (1986)) in pUC 19 vector, bar coding region is driven by a constitutive CaMV 35S promoter followed by the 3' untranslated region and polyadenylation signal of the nopaline synthase gene (nos) (Bevan, M., et al., Nucleic Acid Res. 11 369–385 (1983)), pin2 coding region is driven by the wound-inducible pin2 promoter and rice actin 1 5' intron followed by pin2 terminator. pTW-a is available from Professor Ray Wu of Cornell University, Ithaca, N.Y. The plasmid has been deposited under the Budapest Treaty with the American Type Culture Collection, 12301 Parklawn Drive, Rockville, Md. 20852 as ATCC 97986.

The plasmid pAct-F (6.5 kb; McElroy, D., et al., Plant Cell 2 163–171 (1990)) contains the reporter marker gene, uidA(gus) (Jefferson, R. A., Plant Mol. Biol. Rep. 5 387–401 (1987)), driven by the 5' region of the rice actin 1 gene (McElroy, D., et al., Plant Cell 2 167–171 (1990)) and followed by the nos 3' terminator in pBluescript KS vector. pAct-F is available from Professor Ray Wu of Cornell University, Ithaca, N.Y.

The plasmid DNA was suspended in 10 mM Tris-HCl and 1 mM EDTA buffer (pH 8.0) at a concentration of 1 µg/ml.

Microprojectile bombardment

Plasmid DNA was precipitated onto gold particles (1.0 and 1.6 µm in diameter; Bio-Rad, Hercules, Calif.) or tungsten particles (0.9–1.2 µm in diameter; GTE Sylvania, Towanda, Pa.) following the original protocol described by Bio-Rad with modification. Briefly, thirty milligrams of the particle were sterilized in 1 ml 100% ethanol under vortexing for 30 minutes. Aliquot 50 µl of particle-ethanol suspension were pipetted into a microcentrifuge tube while vortexing continuously. After washing twice with sterile distilled water, the particles were resuspended in 332 µl of sterile distilled water, then successively added 15 µl plasmid DNA (15 µg of plasmid or a 1:1 mixture of two plasmids), 225 µl $CaCl_2$ (2.5M), and 50 µl spermidine (1M) under vortexing at room temperature. The mixture was continuously vortexed for 5 minutes, then set in ice for 15 minutes. The DNA-coated particles were pelleted by centrifuging at 13000 rpm for 1 minute. After discarding the supernatant, the particles were washed with 500 µl absolute ethanol by vortexing for 30 seconds, centrifuging for 1 minute, removing the supernatant, and finally resuspended in 100 or 200 µl absolute ethanol. For each bombardment, aliquot 10 µl of the particle suspensions (150 µg or 75 µg per shot, respectively) were pipetted onto the center of the macrocarriers. The prepared macrocarriers were used as soon as the ethanol evaporated.

Prior to bombardment, shoot tips or shoot-tip clumps from the different culture stages were physically exposed by removal of the coleoptile and leaves if necessary. After gathering on the multiplication medium solidified with 0.5% phytagel in Petri dish, the target materials (about 1.5 cm in diameter) were positioned below the microprojectile stopping screen.

Bombardments were carried out using a Biolistic particle acceleration derive (PDS 1000/He, Bio-rad under 26 mm Hg chamber pressure at a distance of 1.5, 2.0 and 6.5 cm among the rupture disc-macrocarriers-stopping screen-target, with three helium pressures (1100, 1550 and 1800 psi).

Selection and regeneration of transformants

For analyzing the variation of stable expression in shoot tips among the genotypes, the bombarded materials were immediately transferred to the fresh multiplication medium without selection agent, glufosinate ammonium (GF) for six weeks with one subculture.

For recovery of the transformants, the bombarded shoot-tip clumps were cultured on the multiplication medium CSMD for four weeks. The clumps then were divided and subcultured on CSMD but replaced CH with 3 mg/l glufosinate ammonium, designed as CSMD3GF for four weeks. Subsequent subculture at four-week intervals were carried out by selecting, dividing, and culturing the green clumps on CSMD containing 5 mg/l glufosinate ammonium, designed as CSMD5GF.

The regeneration of plants was obtained by transferring the shoot-tip clumps to MS medium-containing 2.25 µM BA, 1.8 µM indole-3-butyric acid (IBA) and 5–10 mg/l glufosinate ammonium. Developed shoots were rooted on MS medium containing 3.6 µM IBA and 10 mg/l glufosinate ammonium. Plantlets then were transplanted into a soil mixture composed of 1:1(V:V) peat and perlite and further developed to maturity.

Induction of in vitro multiple ears and in vivo multiple-ear plants

The herbicide-selected multiple shoot clumps cultured on the multiplication medium were isolated and subcultured on the ear-induction medium containing 4.5 µM BA and 5 mg/l glufosinate ammonium for in vitro multiple ear induction.

For in vivo multiple-ear induction, the shoots regenerated on MS medium containing 2.25 µM BA and 1.8 µM IBA were cultured on MS medium containing 4.5 µM BA and 5 mg/l for two weeks, then transferred to MS medium containing 3.6 µM IBA for root induction, both supplemented with 10 mg/l GF. The plantlets were transferred to soil for further development.

Histochemical and fluorometric assay of β-glucuronidase

The modified histochemical assay buffer consisted of 100 mM $NaPO_4$ buffer, 100 mM EDTA, 50 mM ferrocyanide, and 0.1% Triton X-100 (pH 7.0). X-glucuronide (Clontech Laboratories, Inc.) was pre-dissolved in 50% ethanol stored at 20° C. and added to buffer at a final concentration of 0.5 mg/l prior to assay.

The fluorometric assay buffer consisted of 50 mM $NaPO_4$ buffer, 10 mM β-mercaptoethanol, 10 mM $Na_2$ EDTA, 0.1% sodium lauryl sarcosine and 0.1% Triton X-100. 4-methylumbelliferyl β-D-glucuronide (MUG) were added to buffer at a final concentration of 1 mg/ml prior to assay. All tissues, organs and plantlets were imbued with GUS substrate mixture immediately followed by vacuuming for 10 minutes, then incubated 2 hours at 37° C. The histochemical and fluorometric localization of β-glucuronidase activity were carried out by incubation of hand-cross sections or shoot apexes for 20 minutes at 37° C.

The bombarded shoot-tip clumps were observed under a stereomicroscope. The total stable transformed cells from each bombardment were scored. A single isolated or an aggregate of cells exhibiting dark blue color in the shoot apices other than in the leaves was considered as one stable transformed cell. Before the pictures were taken, the chlorophyll was extracted by successive incubation of 70% and 100% ethanol for 2 hours and overnight, respectively.

Phosphinothricin acetyltransferase (PAT) activity assay

To confirm the PAT activity, twice application of IGNITE non-selective herbicide (AKA BASTA; Hoeschst-Roussel Agri-Vet Company, N.J.) containing 200 mg/l of glufosinate ammonium (phosphinotricin), the active ingredient.

Figure 4A:
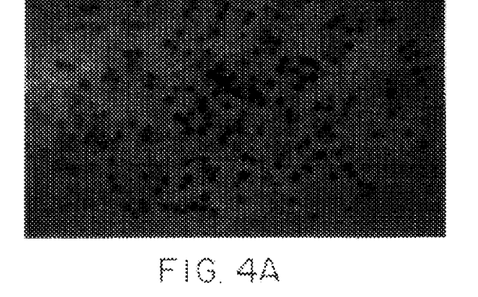
FIG. 4A is a photograph showing the pattern of gus expression in the mature pollen grains.
Figure 4B:
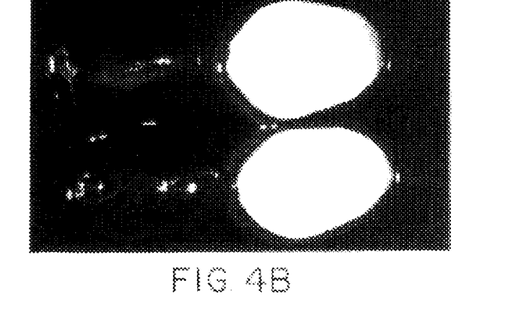
FIG. 4B is a photograph showing the segregation of gus expression in the immature embryos.
Figure 4C:
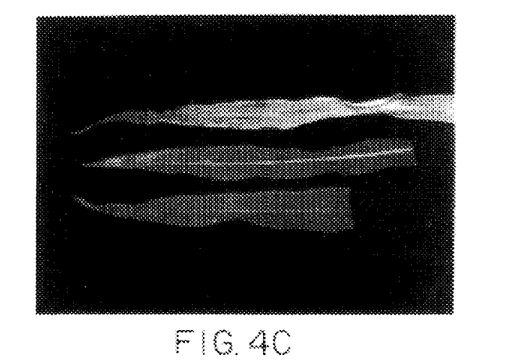
FIG. 4C is a photograph showing the initial screening of R1 plants for bar gene which were performed by painting of leaves with 2 mg/l IGNITE. upper: control non-transgenic. lower: transgenic.
Figure 4D:
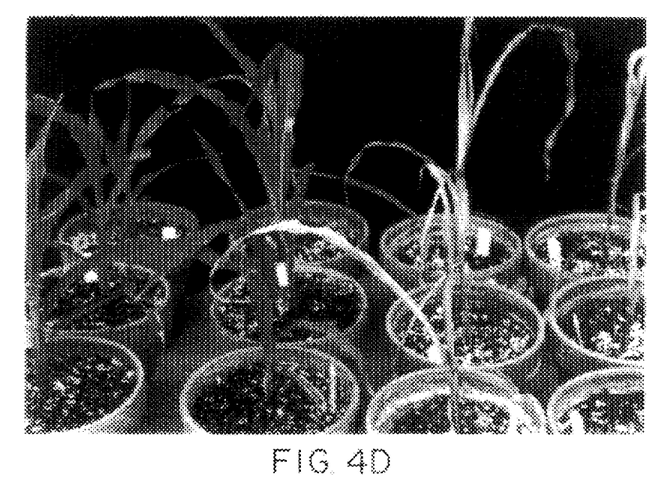
FIG. 4D is a photograph showing the segregation (1:1) of the bar gene in R1 plants.

For R0 plants, 1% of herbicide was sprayed on whole plants at three-leaf and six-leaf stage at greenhouse. For R1 plants, 2% of herbicide was locally painted on youngest leaf at three-leaf stage and sprayed on whole plants at six-leaf stage (FIGS. 4C and 4D).

DNA gel blot analysis

Figure 5A:
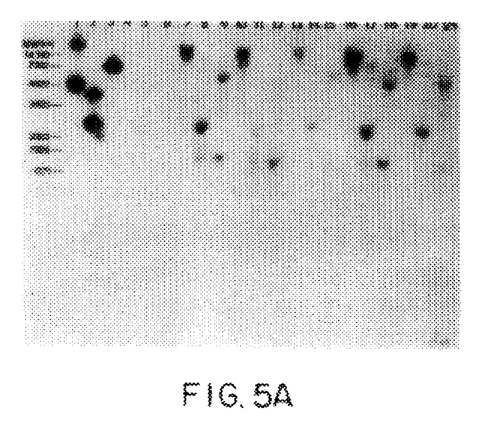
FIGS. 5A and 5B are southern blots of R0 transgenic plant containing both bar and pin2 genes.
Figure 5B:
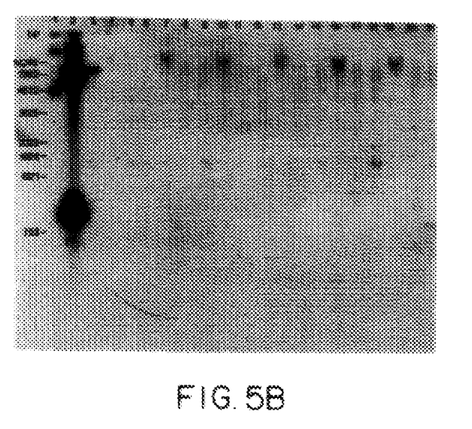
Figure 5C:
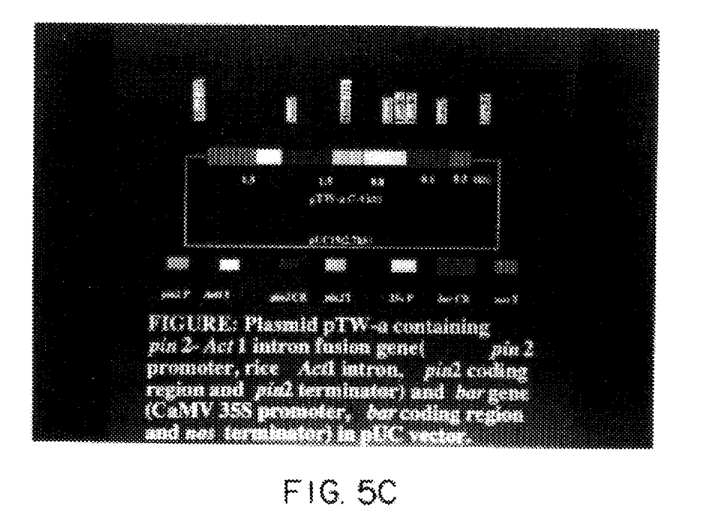
FIG. 5C is a photograph showing the pTW construct used in the experiment.

Genomic DNA was isolated from leaf tissues. Ten micrograms of DNA per sample were digested with restriction enzymes, fractionated in a 1% agarose gel, and transferred to Nytran membrane (Scheicher & Schuell, Inc., Keene, N.Y.). Following the procedure recommended by Scheicher & Schuell, Inc., the pre-hybridization and hybridization were carried out with $\alpha^{32}$P-dCTP probe labeled as described by Pharmacia (Piscataway, N.J.) (T7 QUICK PRIME) (FIG. 5A and FIG. 5B).

Production, analysis and multiplication of progeny

The transgenic plants were self-pollinated. The Screening of transgenic progenies were carried out either using the embryo rescue technique by dissecting from young caryopses and cultured on MS basal medium or multiplication medium with 3 mg/l glufosinate ammonium for minimizing the time and maximizing the amount required to obtain transgenic R1 and R2 plants, or using herbicide application technique to select greenhouse-germinated progeny. The segregation was analyzed with both techniques.

EXAMPLE 1

Genotype-independent stable expression of gus in shoot tips after bombardments

Figure 1A:
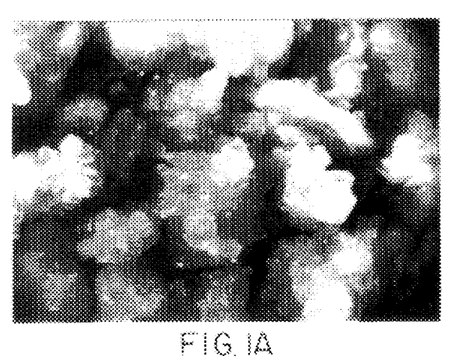
FIG. 1A is a photograph showing shoot meristems prior to bombardment.

The physical exposure of shoot tips from the young maize seedling are extremely difficult and time-consuming, and also the damage on the shoot tip always resulted in the abortion of shoot-tip development. Serial experiments on the attempt of bombarding unexposed shoot tips using GUS as a visible marker revealed that the most expression events happened on the leaves which covered the shoot tip or developed from leaf primordia. Almost no expression was observed in shoot tip after the further development of shoot-tip explants without multiplication (data not shown). Therefore, the explants using bombardment were one-month old or longer cultured shoot tips (FIG. 1A).

Figure 1B:
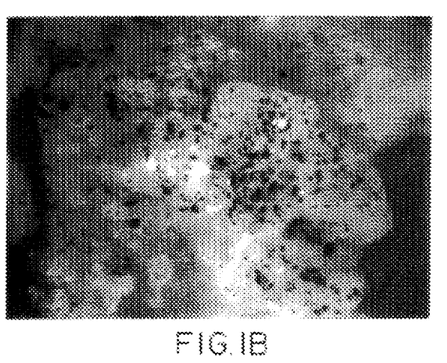
FIG. 1B is a photograph showing the transient expression (blue foci) of gus in the shoot tips of maize two days after bombardment with pActl-F.
Figure 1C:
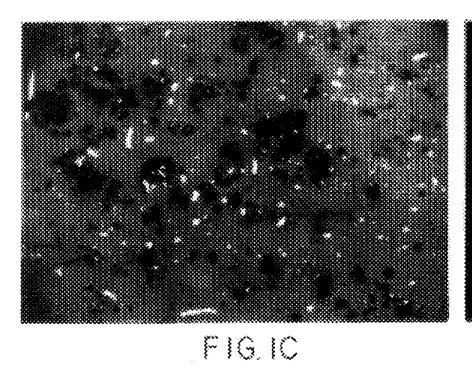
FIG. 1C is a photograph showing the transient expression (blue foci) of gus in the maize type II embryogenic calli two days after bombardment with pActl-F.

In order to address the genotype-independent issue, there was a focus on the stable expression instead of the transient expression in the shoot tip although the transient expression of GUS gene in shoot tip of maize were comparable to that in the type II embryogenic calli and immature embryos of maize (FIGS. 1B and 1C). For ensuring the bombardment performances and grading the level of transient expression, one to three bombarded samples from each experiment were assayed on day after bombardment.

A preliminary study to determine the stable expression cells using the multiple shoot tips of HNP showed that there was little change in terms of amount of blue foci in shoot-tip clumps between three weeks and three months after bombardment. Therefore, the expression of GUS gene in shoot tips six weeks after bombardment was considered to be stable.

EXAMPLE 2

Optimizing the bombardment parameters is always the prerequisite for microprojectile bombardment. Based on preliminary experiments, the physical parts of particle gun were set up as described in methods for minimizing the damage of gas blast and acoustic shock on the shoot tips. The effects of particle size and quality, acceleration pressure and number of shots on stable expression of GUS gene in shoot tips of different genotypes are summarized in Table 1.

TABLE 1

| Geno-type | Parameter[a] | Total No. of shoot tips[b] | Transient express -ion[c] | No. of blue foci/Exp.[d] |
|---|---|---|---|---|
| HNP | 1.0 G + 1100 + 150 + 1 | 633 (4) | ++ | 30.5 ± 5.5 (19) |
| | 75 + 2 | 509 (3) | ++ | 37.3 ± 6.4 (22) |
| | 4 | 723 (5) | +++ | 36.0 ± 6.0 (25) |
| | 1.0 G + 1550 + 150 + 1 | 421 (3) | ++ | 28.7 ± 5.3 (20) |
| | 75 + 2 | 556 (4) | +++ | 37.3 ± 6.1 (27) |
| | 1800 + 75 + 2 | 441 (3) | ++ | 13.7 ± 3.7 (9) |
| | 1.6 G + 1100 + 150 + 1 | 664 (5) | ++ | 9.0 ± 3.0 (7) |
| | 75 + 2 | 370 (3) | +++ | 11.0 ± 3.4 (9) |
| | 1550 + 75 + 2 | 613 (5) | ++ | 10.4 ± 3.1 (8) |
| | 1800 + 150 + 2 | 636 (5) | + | 3.0 ± 1.6 (2) |
| | 1.0 T + 1100 + 75 + 2 | 722 (4) | +++ | 18.3 ± 4.2 (10) |
| | 1550 + 150 + 1 | 834 (6) | ++ | 22.2 ± 4.7 (16) |
| | 150 + 2 | 925 (8) | +++ | 13.1 ± 3.6 (11) |
| | 75 + 2 | 821 (6) | +++ | 32.0 ± 8.5 (23) |
| | 75 + 4 | 1055 (8) | +++ | 42.4 ± 6.5 (32) |
| | 1800 + 75 + 1 | 751 (4) | + | 30.0 ± 5.5 (16) |
| IGXS | 1.0 T + 1550 + 75 + 3 | 423 (3) | +++ | 35.7 ± 5.9 (25) |
| | 1.0 G + 1550 + 75 + 4 | 666 (5) | +++ | 35.6 ± 2.7 (27) |
| 509 | 1.0 T + 1550 + 75 + 2 | 612 (5) | +++ | 21.0 ± 4.6 (17) |
| | 1.6 G + 1800 + 75 + 2 | 511 (4) | ++ | 10.3 ± 6.8 (8) |
| A188 | 1.0 G + 1550 + 75 + 4 | 411 (4) | +++ | 29.8 ± 5.5 (29) |
| | 1.6 G + 1800 + 75 + 2 | 334 (3) | ++ | 6.0 ± 2.3 (5) |

[a]Parameter 1.0 G (or T) + 1100 + 150 + 1 represents the bombardment condition is; 1.0 μm gold (or tungsten) particle, 1100 psi acceleration pressure, 150 μg particle density per shot and one bombardment, respectively.
[b]The number in parenthesis represents the number of experiment in terms of individual petri dishes.
[c]Transient expression grade was rated visually according the number of blue foci in each bombarded sample as +++ for over 800, ++ for 200–800 and + for less than 200.
[d]The data represents the means ± stand error. The number in parentheses represents the relatively efficiency (%) of stable expression measured as total blue foci divided by total number of bombarded shoot tips.

Figure 1D:
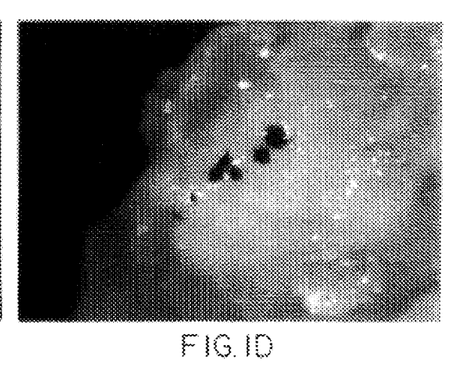
FIG. 1D is a photograph showing the five individual events with stable expression of gus in a single shoot tip.

The efficiency of both transient and stable expression in shoot tips were greatly affected by the penetration of particles which depended on the size, quality, density and velocity of particles. The increasing of the stable expression efficiency were most likely to correspond to the density of particles per shot. The higher transient expression did not always relate to the highest efficiency of stable expression. The larger gold particles (1.6 μm) incorporated with higher density and multiple bombardments under 1800 psi acceleration pressure showed the lowest transient and stable expression, but reducing the particle density and/or acceleration pressure relatively improved the efficiency of stable expression from 0.5% to 14%. The highest transient expression with much lower stable expression efficiency implicated the lower cell survival rate. The great damage and aborted development of shoot tips were frequently observed in these bombardments. Using the smaller gold particles, the most efficient stable expression event was reached by mediate velocity (1550 psi) with multiple shots (up to 4) following the acceleration of lower density of particles (75 pg/shot). The tungsten particles gave comparable results to the gold particles, although the gold particles produced slightly higher efficiency. Of equal amount of particles per treatment, the lower density of particles with multiple shots gave the higher stable expression ratio than the higher density of particles did regardless of single or multiple shoot(s). Although the relative efficiency of stable expression in shoot tips varied from 0.5% to 48% and the transient expression was uniformly distributed in each experiment, the blue foci were mostly observed out of the center of the target six weeks after bombardment, implicating the possibility of lower survival or higher damage of the central tissues or cells. Up to five blue foci showing the stable expression were found in a single shoot tip (FIG. 1D).

In order to localize the position of stable expression cells in the shoot tips, the tissue with blue foci were carefully dissected and examined under microscope. From about 530 examined tissues from the shoot tips, the percentage of blue foci existed below the epidermal were about 65 and 72% bombarded with gold or tungsten particles with 1550 psi pressure, respectively, and about 22% and 10% with gold or particles with 1100 psi, respectively. This indicated the gold particles penetrated into deeper cell layers than tungsten, particularly under low acceleration pressure.

EXAMPLE 3

Table 2 summarized results which related to physiological parameters of cells in the shoot tips from over two year's research.

TABLE 2

| Geno-type | Parameter[a] | Total No. of Shoot tips[b] | Transient Expression[c] | No. of blue foci/Exp.[d] |
|---|---|---|---|---|
| HNP | 1.0 G + 1 + 1 + CSMD + A | 231 (4) | ++ | 11.5 ± 3.4(20) |
| | 1 + 2 + CSMD + A | 210 (2) | +++ | 13.5 ± 3.7(13) |
| | 2 + 0 + CSMD + A | 378 (3) | +++ | 14.0 ± 3.7(11) |
| | 2 + 1 + CSMD + A | 726 (5) | +++ | 43.4 ± 6.5(30) |
| | 4 + 1 + CSM + A | 197 (2) | +++ | 25.5 ± 5.0(26) |
| | 6 + 0 + CSMD + A | 372 (3) | +++ | 10.0 ± 2.9 (8) |
| | 1.0 T + 2 + 4 + CSMD + A | 214 (2) | +++ | 29.0 ± 5.4(27) |
| | 6 + 2 + CSMD + A | 341 (2) | +++ | 51.0 ± 7.1(30) |
| | 12 + 2 + CSMD + A + B | 461 (3) | +++ | 21.7 ± 4.7(14) |
| EGXS | 1.0 G + 6 + 1 + CSM + A | 294 (2) | +++ | 33.5 ± 5.8(23) |
| | 12 + 2 + CSMD + A + B | 384 (3) | ++ | 20.3 ± 4.5(16) |
| | 24 + 1 + CSMD + A | 443 (3) | +++ | 39.7 ± 6.3(27) |
| | 1.0 T + 1 + 2 + CSM + A | 224 (4) | ++ | 8.5 ± 2.9(15) |
| | 2 + 1 + CSMD + A + B | 324 (3) | ++ | 15.0 ± 3.9(14) |
| 5922 | 1.0 G + 1 + 1 + CSMD + A | 199 (4) | +++ | 7.0 ± 2.6(14) |
| | 1.0 T + 2 + 1 + CSMD + A | 332 (4) | +++ | 14.3 ± 3.8(17) |
| 482 | 1.0 G + 2 + 2 + CSM + A | 173 (2) | +++ | 18.0 ± 4.2(21) |
| | 1.0 T + 2 + 2 + CSMD + A + B | 271 (3) | + | 11.7 ± 3.4(13) |
| B73 | 1.0 G + 4 + 2 + CSM + A | 260 (2) | +++ | 25.5 ± 5.0(20) |
| | 4 + 0 + CSMD + A | 198 (2) | +++ | 10.5 ± 3.3(11) |
| VA22 | 1.0 T + 1 + 1 + CSMD + A + B | 321 (5) | + | 5.0 ± 2.2 (8) |
| FR632 | 1.0 T + 4 + 1 + CSMD + A | 421 (4) | +++ | 29.5 ± 5.4(28) |
| L6 | 1.0 T + 2 + 2 + CSMD + A | 294 (3) | +++ | 23.7 ± 4.9(24) |
| L9 | 1.0 T + 4 + 1 + CSMD + A | 163 (2) | +++ | 18.0 ± 4.2(22) |
| K1 | 1.0 T + 2 + 0 + CSMD + A | 89 (2) | +++ | 5.5 ± 2.3(12) |

TABLE 2-continued

| Geno-type | Parameter[a] | Total No. of Shoot tips[b] | Transient Expression[c] | No. of blue foci/Exp.[d] |
|---|---|---|---|---|

[a]Parameter 1.0 G (or T) + 1 + 1 + CSMD (or CSM) + A (or A + B) represents the bombardment condition is 1.0 μm gold (or tungsten) particle, one-month-old cultures after initiation of culture, one week after subculture in fresh medium, culture medium CSMD (or CSM) and with pct1-F (or in 1:1 ratio of pAct1-F and pTWa), respectively, the physical parameters were 1550 psi acceleration pressure, 75 μg particle density per shot and four times bombardments.
[b]The number in parentheses represents the number of experiment in terms of individual petri dish.
[c]Transient expression grade was rated visually according the number of blue foci in each bombarded sample as +++ for over 800, ++ for 200–800 and + for less than 200.
[d]The data represents the means ± stand error. The number in parentheses represents the relatively efficiency (%) of stable expression measured as total blue foci divided by total number of bombarded shoot tips.

The initiation of shoot tip clumps mostly happened in two to four weeks. Repeated subculture of these shoot tip clumps resulted in the higher frequency of shoot tip formation accompanied with more compact shoot tip clusters. Morphologically, the shoot tips produced in CSMD were relatively more with less leaf elongation than that produced in CSM. After bombardment, the shoot tips from one-month old cultures showed much less efficiency of stable expression although the transient expression were as high as that from older cultures. However, there was a dramatic difference between the shoot tips maintained in the medium for four weeks than the ones just subcultured for one or two weeks. Those results pointed out that the efficiency of stable expression corresponded more to the subcultural frequency than to how long the cultures had been established. The frequent subculture possibly maintained certain physiological status of the cells in shoot tips such as higher activity of division, which could more advantageously condition the cells for the reception of foreign gene.

There was no significant effect on the transient and stable expression between the two kinds of medium, CSM and CSMD, although the shoot tip multiplication was stimulated by the presence of low levels of 2,4-D. Genotypes did not cause any significant difference in terms of transient and stable expressions.

The above data indicated that the optimal delivery of DNA into subepidermal cells of shoot tips were efficiently carried out by the bombardment of more than two-month old shoot tip clumps which had been frequently subcultured, using lower density (75 μg/shot) of 1.0 μm gold or tungsten particles with multiple shots (4 shots) under 1550 psi acceleration pressure. HNP and IGXS were chosen for recovery of transformants under above transformation parameters since they were the model material of morphogenesis study and their shoot tip clumps were regularly initialed and continuously subcultured for more than four years so far without loss of any regeneration ability and fertility of plants. Besides, the reaction of genotypes to bombardment and multiplication of the shoot tips was not much different.

EXAMPLE 4

Figure 1E:
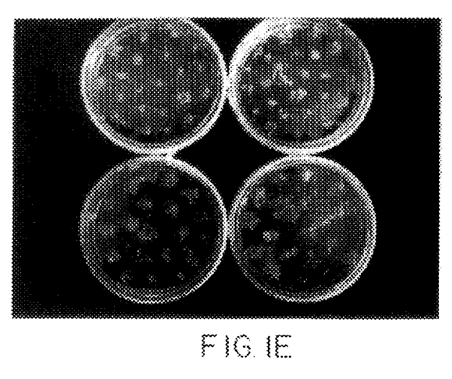
FIG. 1E is a photograph showing the process of selection with 3 mg/l glufosinate ammonium after being transformed with pTW-a. a) control shoot-tip clumps one month after selection; b) transformed shoot-tip clumps one month after selection; c) transformed shoot-tip clumps two months after selection; d) transformed shoot-tip clumps three months after selection.

Transformation with pTWa alone or with pAct1-F The results from 8 independent experiments with total of 22 plates after transformation with plasmid pTWa are summarized in the section A of Table 3 and FIG. 1E. The efficiency for the recovery of resistant shoot tip clumps after first round of selection (one month) with 3 mg/l GF was varied from 0 to 6.7% under different period of post-culture.

Six independent experiments on co-transformation of two unlinked genes gave the relatively low efficiency of recovery of resistant shoot tip clumps after pre-selection, ranging from 0 to 3.4%, as compared to the two linked gene transformation (the section B of Table 3).

the end of third to fourth round selection (1 month in CSMD3G and 3 months in CSMD5G). One independent shoot tip clumps from pre-selection were multiplied to about 15 shoot tip clumps in 5 months after bombardment, capable of regenerating more than 1500 transgenic plantlets.

All GF-resistant clumps were further subjected to DNA hybridization analysis for the present of bar and pinII. The

TABLE 3

| Geno-type | Exp. | No. of plates | Total No. of shoot tips | Days of post-culture[a] | No. of GF-resistant Clumps | | |
|---|---|---|---|---|---|---|---|
| | | | | | pre-selection[b] | post-selection[c] | bar+/pinII+/gus+/GUS+[d] |
| A. | | | | | | | |
| HNP | 1 | 4 | 622 | 3 | 0 | | |
| | 2 | 2 | 181 | 3 | 1(0.2) | 13 | 1/1(100) |
| | 3 | 2 | 284 | 30 | 19(6.7) | 15.1 ± 3.9 | 19/19(100) |
| | 4 | 3 | 291 | 30 | 16(5.5) | 17.1 ± 4.1 | 16/16(100) |
| | 5 | 4 | 560 | 30 | 21(3.8) | 16.9 ± 4.2 | 21/21(100) |
| IGXS | 6 | 3 | 412 | 30 | 15(4.2) | 12.6 ± 3.5 | 15/15(100) |
| | 7 | 2 | 219 | 30 | 9(4.1) | 11.6 ± 3.4 | 9/9(100) |
| | 8 | 2 | 260 | 30 | 14(5.4) | 15.4 ± 3.9 | 14/14(100) |
| subtotal | 8 | 22 | 2829 | | 95 | | |
| B. | | | | | | | |
| HNP | 9 | 2 | 312 | 3 | 0 | 0 | |
| | 10 | 3 | 421 | 30 | 13(3.1) | 12.2 ± 3.5 | 13/13(100)/11(100)/10(77) |
| | 11 | 2 | 194 | 30 | 5(2.6) | 11.0 ± 3.3 | 5/5(100)/4(80)/2(40) |
| IGXS | 12 | 5 | 607 | 30 | 21(3.4) | 14.3 ± 3.8 | 21/21(100)/16(76)/11(52)* |
| | 13 | 3 | 377 | 30 | 9(2.4) | 12.5 ± 3.5 | 9/9(100)/7(78)/4(44) |
| | 14 | 2 | 201 | 30 | 3(1.5) | 13.7 ± 3.7 | 3/3(100)/3(100)/2(67) |
| subtotal | 6 | 17 | 2112 | | 51 | | |

[a]Post-culture day was days after bombardment.
[b]No. of clumps after pre-selection were the total independent clumps obtained at the end of one month selection. The number in parentheses represents the relatively efficiency (%) of stable transformation measured as total GF-resistant clumps divided by total numbers of bombarded shoot tips.
[c]No. of clumps after four-month post selection were means ± stand errors collected based on multiplication of individual GF-resistant clumps from pre-selection. Each clump contained 100 to 150 visible shoot tips.
[d]The number in bar+/pinII+/gus+/GUS+ represents the numbers of independent clumps presented the genes. The number in the parentheses represents the frequency of co-transformation or co-expression measured as total number of clumps contained pinII and gus gene or showed GUS activity divided by total numbers of independent bar-contained clumps.
*Two clumps were presented with partial Gus activity.

The results indicated the one-month post culture of bombarded shoot tip clumps is necessary in order to have higher efficiency of transformation. More than one-month post-multiplication did not improve the recovery of resistant shoot tip clumps. During the first month selection, most shoot tip clumps turned brown beginning in two weeks as it happened to the control clumps. The small group of GF-resistant shoot tips were clearly emerged in a healthy greenish color from those brown tissue at the end of first month pre-selection. The shoot tip clumps from control experiments rarely survived in this selection scheme. The size of the GF-resistant clumps were varied from less than 0.1 cm³ to 0.3 cm³ containing about 5 to 20 visible shoot tips. Since the multiple shoot tip clumps were compact, the intimate signal communication and substance exchange between cells in the clumps provided great possibility of cross-protection between transformed cells and non-transformed cells. Further selection of transformed shoot tip clumps devoid of non-transformed cells was carried out by dissected, divided and cultured the survival shoot tips on CSMD5G until all divided shoot tip clumps uniformly survived in the CSMD5G. Those clumps resistant to 5 mg/l GF were also of resistance to 10 mg/l GF. In both HNP and IGXS, the stable uniform growth clumps were obtained at transformation efficiency of two linked genes was 100% in both transformation and co-transformation experiments. Of the 51 GF-resistant clumps analyzed, 41 clumps contained both bar and gus. The co-transformation frequency of two unlinked genes (bar and gus) was about 83% in average. The histochemical assay of GUS activity and the PAT activity assay of all independent transgenic clumps revealed about 56% of co-expression frequency of two unlinked genes.

Regeneration of transformants

Figure 1F:
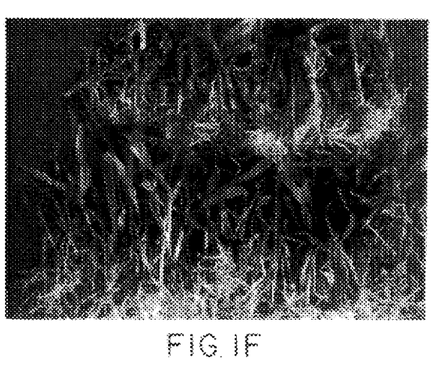
FIG. 1F is a photograph showing in vitro selected plantlets produced from one bombarded shoot meristem.

More than twenty thousand plantlets were successively regenerated from one tenth of GF-resistant clumps in regeneration medium containing 10 mg/l of glufosinate ammonium. All plantlets were healthy and survived (FIG. 1F). The 600 plantlets regenerated from 10 independent transgenic events were transferred to greenhouse for further development. About 90% of them were surveyed and flowered normally (FIGS. 2A, 2B, 2C and 2D).

EXAMPLE 5

Induction of in vitro multiple ears and in vivo multiple-ear plants

Figure 2A:
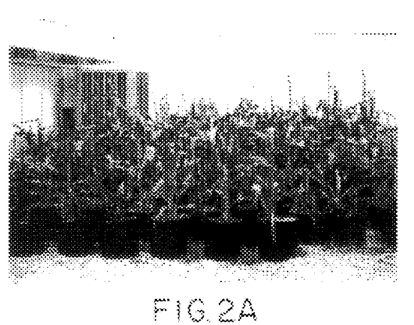
FIG. 2A is a photograph showing the five-hundred transgenic plants in greenhouse produced from one bombarded shoot meristem.
Figure 2B:
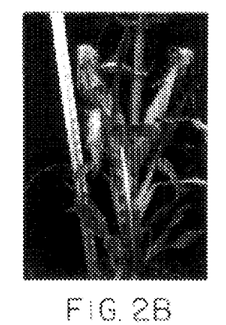
FIG. 2B is a photograph showing the normal development of ears from transgenic plants.
Figure 2C:
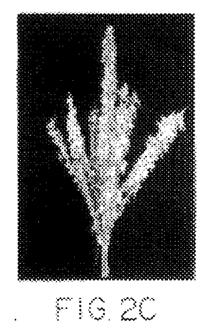
FIG. 2C is a photograph showing the normal development of tassel from transgenic plants.
Figure 2D:
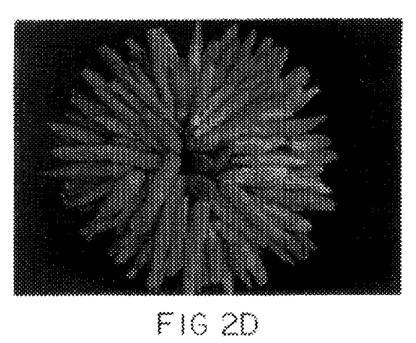
FIG. 2D is a photograph showing the ears with kernels/seeds produced from one bombarded meristem.
Figure 2E:
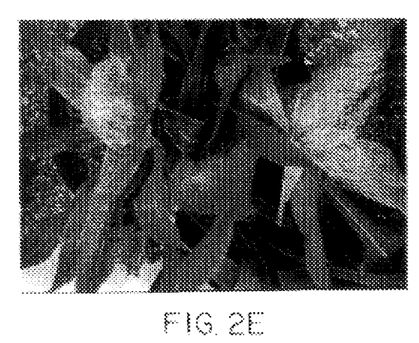
FIG. 2E is a photograph sowing the in vitro multiple ear structure produced from a transgenic shoot tip.

Thirteen resistant shoot tip clumps from Experiment 3 were selected from the in vitro ear induction. Over 78% of them responded to the induction in two months under the selection of 5 mg/l GF. The amount of ears induced from individual small clumps containing 3–5 shoot tips were most produced 6–12 conical ear-like structures. Some of them produced as many as 26 such structures (FIG. 2E). Those presumptive ears further developed into rooted ear-forming shoots in vitro containing about 25 ovaries with normal silks after separated and cultured on the MS medium containing 3.6 μM IBA and 1.0 μMBA.

Figure 2F:
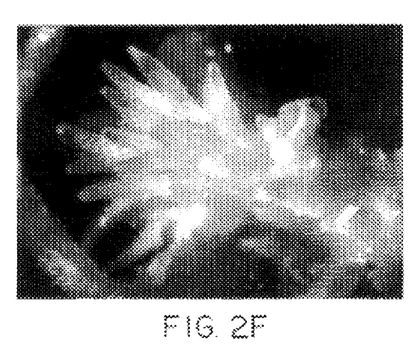
FIG. 2F is a photograph showing the transgenic plant with multiple terminal ears.
Figure 2G:
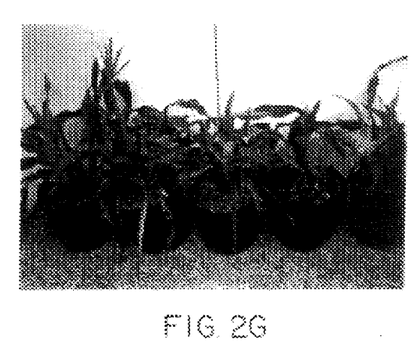
FIG. 2G is a photograph showing the transgenic plants with one shoot tassel and a group of same size terminal ears.
Figure 3A:
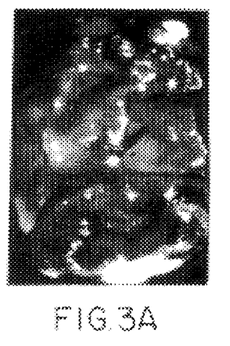
FIG. 3A is a photograph showing the gus expression in the selected shoot tip clump.
Figure 3B:
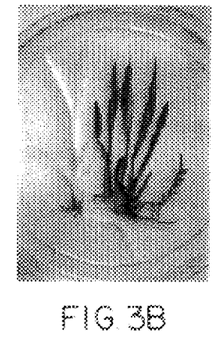
FIG. 3B is a photograph showing the gus expression in the regenerated in vitro transgenic plantlets; left is control non-transgenic plantlet.
Figure 3C:
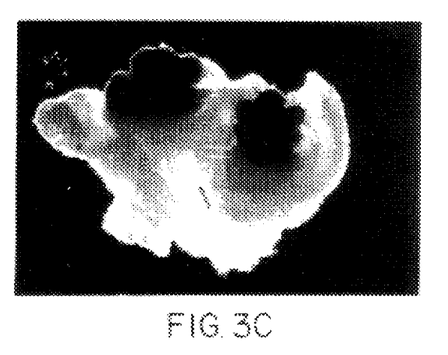
FIG. 3C is a photograph showing the gus expression in the shoot meristems.
Figure 3D:
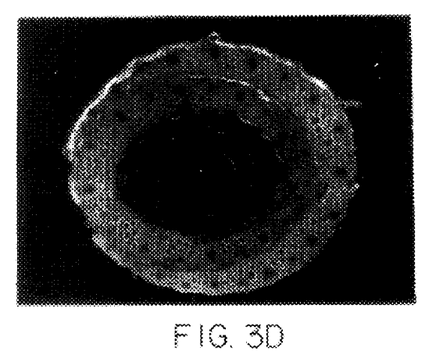
FIG. 3D is a photograph showing the pattern of gus expression the different ages of young leaves.
Figure 3E:
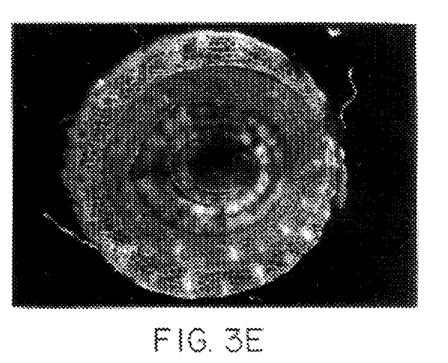
FIG. 3E is a photograph showing the pattern of gus expression in the elongation zone of shoot.
Figure 3F:
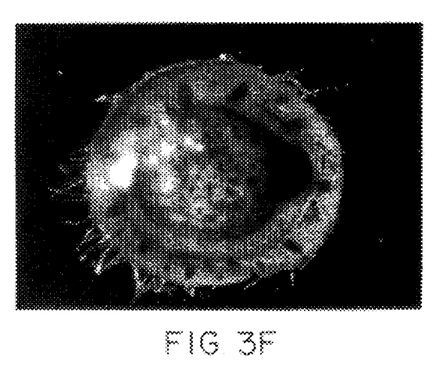
FIG. 3F is a photograph showing the high-level gus expression in the axillary bud.
Figure 3G:
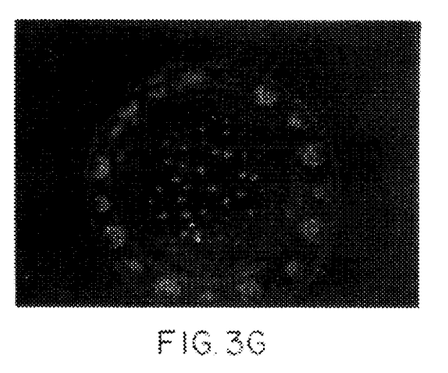
FIG. 3G is a photograph showing the pattern of gus expression in the vascular system of stem.

Thirty-two regenerated plantlets from the GF-resistant clumps of Example 5 were transferred to soil after two-week ear induction on MS medium supplemented with 4.5 μM BA and 5 mg/l GF and two-week root formation on MS medium containing 3.6 μM IBA and 5 mg/l GF. About 5–10 normal ears in each dwarf corn plant were produced in greenhouse. Most of these plants had only multiple terminal ears (FIG. 2F) or had one shoot tassel and a group of same size terminal ears (FIG. 2G). The seeds formed in these plants were normal and had much higher seed production than other regenerated plants. In addition, these plants flowered 1–2 months earlier than regularly regenerated plants.

Analysis of R0 and R1 transgenic plants Histochemical and fluorometric metric localization of β-glucuronidase The visualization of Act1-gus activity pattern in transgenic R0 plants were summarized in FIGS. 3A–3G. FIGS. 4A and 4B. The whole plantlets regenerated from in vitro transgenic and untransformed shoot tip clumps were imbued with X-GLUC-assay buffer mixture. Ten minutes after incubation at 37° C., the root hair presented the first sign of GUS activity, followed by the emergence of blue coloration in the all root tip, secondary root and root elongation zone in 30 minutes. The blue color showed on the younger leaves began from the base of leaves, gradually extending to whole leaves as well as appearing in the older leaf. The whole plantlets turned to intense GUS staining after 3 hours of incubation at 37° C. Further incubation of plantlets caused the assay buffer to turn to blue because of the oxidized substrate released from plantlets. A series of hand-cut cross-section from control and transgenic plants were subjected to histochemical and fluorometric staining in order to localize the cellular pattern of GUS activity. Ten minutes after incubation, the sections were observed under microscope. The highest intense GUS staining were located in the vascular system, shoot and root tip areas and axillary bud. The pattern of Gus intensity in cells were phloem>epidermal cell>mesophyll cell in leaf, phloem>root hair>endodermis>epidermis>cortex in root. The younger the leaf and root, the more intense the blue. Shoot tip including meristem and leaf primordia showed the strongest GUS activity five minutes after exposure to staining buffer.

The reproductive meristem showed as intense blue color as the vegetative meristem, particularly in all spikelet primordia. The pattern in the further developed reproductive organ were floret>glume>anther and silk. Mature flower did not present the gus activity after overnight incubation. The mature pollen showed relatively higher gus activity, but varied among them and presented about 1:1 ratio of GUS positive:negative.

The method of the present invention is of practical utility for both basic and applied development of maize biology. The previously reported systems established for maize transformation were not effective and efficient enough to meet the practical requirement of maize biologists. In addition to the great variation of efficiency in the transformation techniques and methods, the majority of limitations came from the friable embryogenic type II callus formation, the totipotency of protoplasts, the competence of immature embryo and type I callus for regeneration and the possibility and efficiency of co-transformation, which were all genotype-dependent. Moreover, the labor-intensive and the time-consuming in vitro and in vivo manipulation as well as the great possibility of chromosome variation are also highly undesirable. The present invention is based on the concept of morphogenetic plasticity of maize meristem, which provides a major breakthrough for recovery of tremendous amounts of independently transformed fertile maize plants in a short period via the efficient shoot-tip multiplication system with unlimited regeneration ability. The system itself not only has the advantage of particle bombardment which allowed delivery of more than one gene in different plasmid with high frequency (83% in co-transformation and 56% in co-expression), but also is easy practicable and in a genotype-independent fashion. In addition, the explants, shoot tips, were easily and simply obtained from germinated seedling, which had less limitation of time, labor and space as compared to all previous systems. This regeneration system using shoot multiplication from apex meristem provided less chromosome variation than with callus induction. Once the regeneration is established, the uniform explant sources desired by all maize biologists can be provided at any time of the year from the research. Two sweet corn genotypes were maintained for over a four year period with increasing regeneration ability. (FIGS. 5A and 5B bar gene and insects).

It is intended that the foregoing description be only illustrative of the present invention and that the present invention be limited only by the hereinafter appended claims.

We claim:

1. A method for producing a maize plant with foreign DNA encoding a herbicide or insecticide resistance which comprises:

(a) providing isolated shoot apex meristem primordia of germinated embryos of the maize which have been separated from a coleoptile and exposed by removal of leaf primordia of the plant in a first culture medium comprising a cytokinin selected from the group consisting of N₆-benzyladenine, 6-furfurylamino-purine and 6-(4-hydroxy-3-methylbut-2-enylamino)purine at a concentration between about 0.001 to 10 μM and optionally an auxin selected from the group consisting of 3,6-dichloro-o-anisic acid, 2,4-dichlorophenoxyacetic acid, indole-3-acetic acid, indole-3-butyric acid and α-naphthaleneacetic acid at a concentration of between about 0.001 to 10 μM with frequent subculturing over time to enable the meristem primordia to be transformed with the foreign DNA;

(b) bombarding the subcultured meristem primordia with micron sized particles coated with the foreign DNA to transform the meristem primordia with the DNA;

(c) growing the bombarded meristem primordia in a second culture medium containing the auxin and optionally the cytokinin and selecting for transformed meristem primordia using the herbicide; and (d) regenerating the meristem primordia containing the foreign DNA in a culture medium containing the auxin to produce the transformed maize plant which has the herbicide or insect resistance.

2. The method of claim 1 wherein in addition the foreign DNA encodes an enzyme which is used as a visual selection marker.

3. The method of claim 2 wherein the enzyme is β-glucuronidase.

4. The method of claim 1 wherein the first and second culture medium contains casein hydrolysate and $N_6$-benzyladenine and optionally 2,4-dichlorophenoxyacetic acid and the meristem primordia in step (a) are cultured in darkness for four weeks and then in the light for four weeks.

5. The method of claim 4 wherein the first culture medium and second culture medium contain MS medium.

6. The method of claim 5 wherein the first culture medium and second culture medium contain 0.5 to 1 g/liter casein hydrolysate and the 2,4-dichlorophenoxyacetic acid.

7. The method of claim 1 wherein the foreign DNA includes a promoter.

8. The method of claim 7 wherein the promoter is rice actin 1 promoter.

9. The method of claim 8 wherein the foreign DNA includes a 5' intron and a 5' non-coding exon.

10. The method of claim 1 wherein the foreign DNA encodes a bar gene for herbicide resistance.

11. The method of claim 1 wherein the foreign DNA encodes a pin 2 gene for insect resistance.

12. The method of claim 1 wherein the foreign DNA encodes a bar gene for resistance to glufosinate ammonium and a pin-2-gene for insect resistance.

13. The method of claim 1 wherein the foreign DNA is contained in plasmid pTW-a.

14. The method of claim 1 wherein the auxin in step (c) is indole-3-butyric acid (IBA).

15. The method of claim 14 wherein the indole-3-butyric acid is present in an amount between 0.001 and 10 µM.

* * * * *